United States Patent
Durpetti

(10) Patent No.: US 8,388,218 B2
(45) Date of Patent: Mar. 5, 2013

(54) REPLACEABLE DECORATIVE COVER FOR WATCHES WITH DIGITAL DISPLAY

(75) Inventor: Silvia Durpetti, Senigallia (IT)

(73) Assignee: Squan di Pascual Luna Maria Paula & C. Sas, Senigallia (IT)

( * ) Notice: Subject to any disclaimer, the term of this patent is extended or adjusted under 35 U.S.C. 154(b) by 62 days.

(21) Appl. No.: 12/736,589

(22) PCT Filed: Dec. 4, 2009

(86) PCT No.: PCT/EP2009/066465
§ 371 (c)(1),
(2), (4) Date: Oct. 21, 2010

(87) PCT Pub. No.: WO2011/006548
PCT Pub. Date: Jan. 20, 2011

(65) Prior Publication Data
US 2011/0205859 A1    Aug. 25, 2011

(30) Foreign Application Priority Data
Jul. 16, 2009   (IT) .............................. MC2009U0043

(51) Int. Cl.
*G04B 37/00*    (2006.01)
(52) U.S. Cl. ....................................... 368/284; 368/283
(58) Field of Classification Search ................... 368/285, 368/284, 282, 283
See application file for complete search history.

(56) References Cited

U.S. PATENT DOCUMENTS

| | | | | |
|---|---|---|---|---|
| 2,274,207 A * | 2/1942 | Merz | ............................. | 368/282 |
| 3,996,736 A * | 12/1976 | Bodet | ............................. | 368/286 |
| 4,015,422 A * | 4/1977 | Van Haaften | ................. | 368/281 |
| 4,396,298 A | 8/1983 | Ripley | ........................... | 368/300 |
| 4,825,427 A * | 4/1989 | Wollman | ....................... | 368/282 |
| 4,831,606 A * | 5/1989 | Aellen | ........................... | 368/282 |
| 5,034,932 A * | 7/1991 | Grosjean | ....................... | 368/286 |
| 5,142,512 A * | 8/1992 | Takano et al. | ................. | 368/232 |
| 5,206,841 A * | 4/1993 | Boucheron | .................... | 368/276 |
| 6,130,861 A * | 10/2000 | Della Felice | .................. | 368/276 |
| 7,339,856 B1 * | 3/2008 | Hardesty | ........................ | 368/228 |
| 2009/0260394 A1 * | 10/2009 | Heiden et al. | ..................... | 63/3.1 |
| 2011/0032804 A1 * | 2/2011 | Scioscia | ........................ | 368/281 |

FOREIGN PATENT DOCUMENTS

| | | |
|---|---|---|
| EP | 0 276 701 | 8/1988 |
| WO | WO 91/02299 | 2/1991 |

* cited by examiner

*Primary Examiner* — Sean Kayes
(74) *Attorney, Agent, or Firm* — Lowe, Hauptman, Ham & Berner, LLP

(57) ABSTRACT

The present invention relates to a replaceable decorative cover adapted to be snap-coupled with one of those watches formed of a monolithic rubber bracelet provided in the center with a tapering enlarged section that contains the display of the watch.

4 Claims, 2 Drawing Sheets

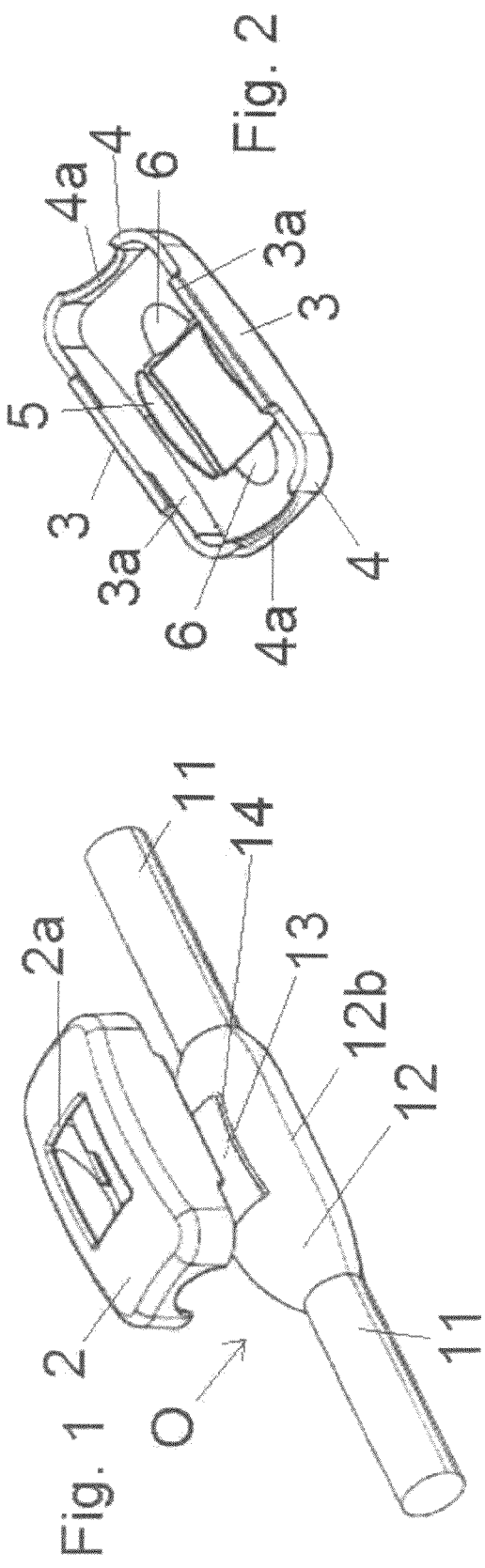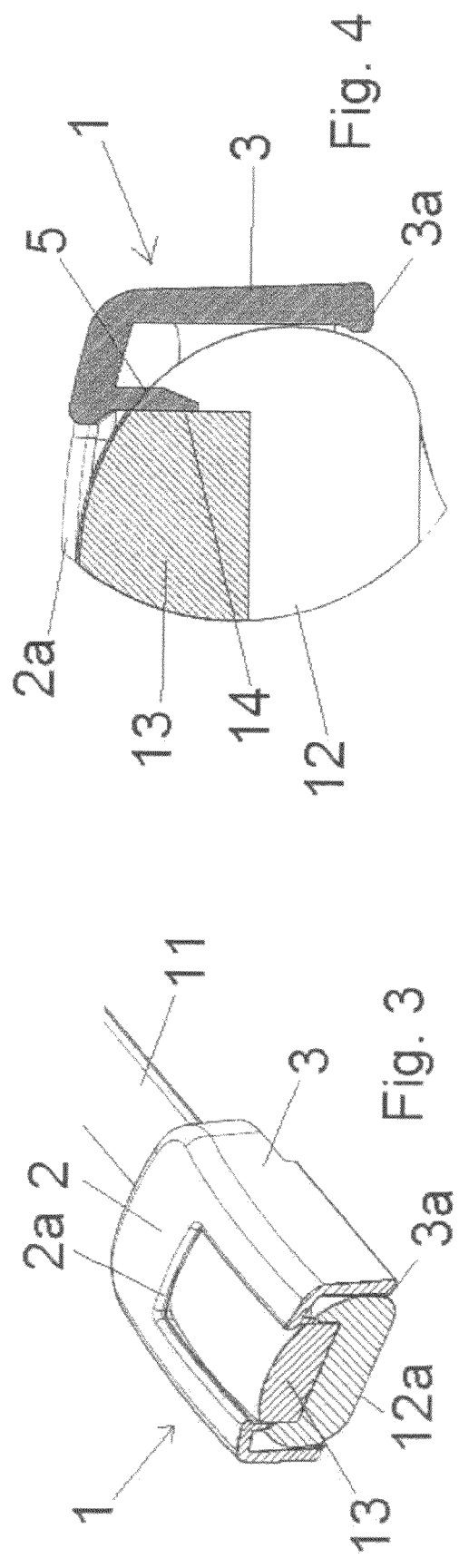

REPLACEABLE DECORATIVE COVER FOR WATCHES WITH DIGITAL DISPLAY

Figure 5:
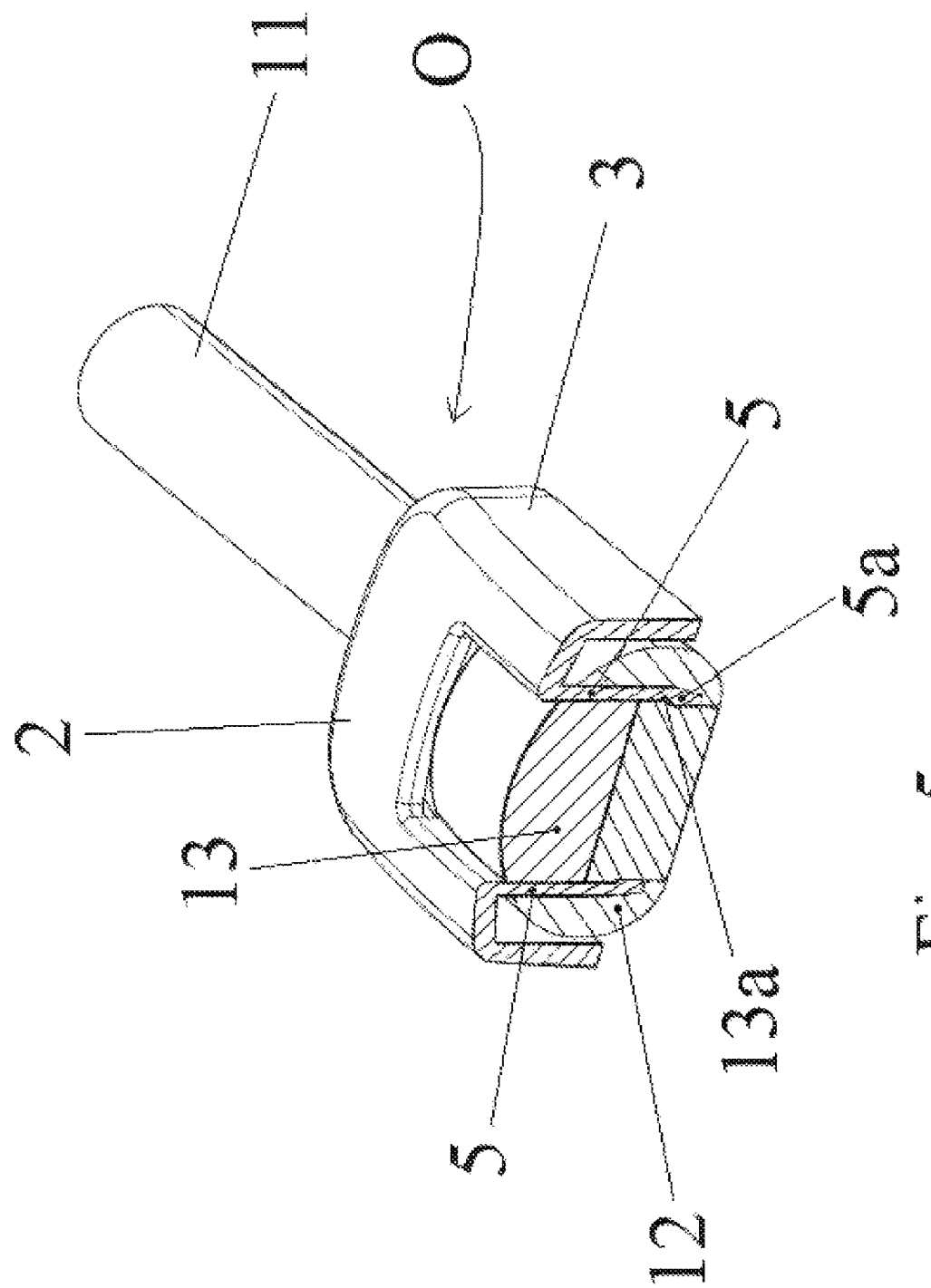

The present patent application relates to a replaceable decorative cover for watches with digital display.

As it is known, a particular type of inexpensive watches with digital face has recently become popular on the market.

Reference is made to watches provided with a thin monolithic rubber bracelet, in which a basically rectangular space is obtained to exactly receive a corresponding block with digital display.

In particular, such a block contains the miniaturised electronic parts used to "calculate" time and show the relevant information on the display for the user.

It must be noted that this type of watches is especially targeted to young and very young customers, who largely appreciate them not only for their essential and inexpensive structure, but also for their capacity to characterise the global look of the user in terms of casual and modern elegance.

A careful examination of the state of the art, however, has identified a disadvantageous aspect of said watches.

In a time when young people tend to change their look continuously, it is possible for users of one of the above digital watches to lose the appreciation because of its well-defined and standardised look.

A further aspect of this problem is related to the fact that, especially if purchased in a version characterised by an especially "bright" colour, such a watch may not match the garments or accessories worn by the user.

The cover of the present invention has been devised further to a careful examination of the prior art, as solution to the aforementioned drawbacks.

It consists in a plastic moulded cover adapted to be easily coupled or uncoupled to or from one of said watches composed of a monolithic bracelet that integrates a small rectangular display.

In particular, the cover is inserted along the bracelet at the height of the rectangular display, in order to surround it completely.

Moreover, said rectangular cover has large dimensions and pronounced corners.

In view of the above, the cover of the invention can considerably affect the general look of the watch, making it less linear and more eye-catching.

It can be otherwise said that, after being coupled with the cover of the invention, such a watch tends to acquire a peculiar appearance that can induce the observer to think that it is not the original watch.

Moreover, the cover of the invention can be produced with any type of colour, in such a way to be purchased by the user from time to time in the desired colour, possibly according to the current fashion taste or the chromatic characteristics of his clothes.

For purposes of clarity, the description of the invention continues with reference to the enclosed drawing, which is intended for purposes of illustration only and not in a limiting sense, wherein:

FIG. 1 is an axonometric view of the cover of the invention above the watch, before coupling FIG. 2 is an axonometric view that illustrates the internal configuration of the cover of the invention FIG. 3 is an axonometric view of a section of the cover of the invention coupled with the watch FIG. 4 is a partial front view of FIG. 3 that illustrates in detail the coupling of the cover of the invention with the watch.

FIG. 5 is basically the same as FIG. 3, except that it refers to an alternative constructive embodiment of the cover of the invention.

Referring to the above figures, the cover of the invention (1) is mounted on a watch (O) of the type composed of a thin monolithic bracelet (11) with circular section, provided with a longitudinal tapering enlarged section (12) with lower flat side (12a).

The upper side of the enlarged section (12) is provided with a basically rectangular space that firmly houses a digital watch formed of a parallelepiped block (13) that contains the necessary electronic parts and is provided on top with a small display with basically rectangular shape and rounded profile from a longitudinal edge to the other edge of the parallelepiped block (13).

The block (13) has a slightly higher height and a slightly lower width than the corresponding housing.

In view of the above, the upper convex section of the block (13), including the display, slightly protrudes from the housing, and narrow longitudinal slots (14) are formed on the two sides of the block (13) as result of possible elastic deformation imposed on the lateral walls of said space.

The cover of the invention (1) can be easily snap-coupled and uncoupled to and from said enlarged section (12) of the watch (O), while leaving the digital display visible.

It consists in a basically rectangular boxed cover moulded from plastic materials and provided with intrinsic flexibility.

The cover (1) is formed of a basically rectangular horizontal wall (2) that is bordered by two opposite pairs of downward edges (3, 4).

The horizontal wall (2) is longitudinally provided with a rectangular window (2a) with shape and dimensions compatible with the display of the watch (O).

Each longitudinal edge (3) of the cover (1) is provided on the lower border with a slightly inward-protruding axial rib (3a), whereas each of the two transversal edges (4) of the cover (1) is provided with a basically semicircular notch (4a).

The height of the four edges of the cover (1) is slightly lower than the enlarged section (12) of the watch (O).

The distance between the two longitudinal edges (3) of the cover (1) is slightly lower than the maximum width of said enlarged section (12) of the watch (O), whereas the distance between the transversal edges (4) is basically equal to the length of the same enlarged section (12).

Referring to FIG. 2, the horizontal wall (2) of the cover (1) is provided with two thin vertical partitions (5) that protrude from the internal side, in slightly more external position with respect to the longitudinal edges of the window (2a).

Likewise, the lower side of the horizontal wall (2) is provided with two s basically semi-elliptical impressions (6) in symmetrically opposite position, having higher width and higher depth on the transversal edges of the window (2a).

After illustrating the structure of the cover of the invention (1), this description continues by explaining the way the cover cooperates with the watch (O).

The cover (1) must be slightly forced from above on the enlarged section (12) of the watch (O).

During the downward movement, the ribs (3a) of the longitudinal edges (3) of the cover (1) gradually interfere with the longitudinal edges of the is enlarged section (12) of the watch (O), causing a slight divarication of the longitudinal edges (3).

The downward movement ends when the lower side of the horizontal wall (2) of the cover (1) touches against the upper side of the enlarged section (12) of the watch (O).

In such a lower stop position, the following simultaneous consequences are noted:

the upper section of the parallelepiped block (13) with display is exactly arranged in the opening of the window (2a) of the cover (1), remaining perfectly visit from outside thereof the two impressions (6) obtained on the lower side of the horizontal wall (2) of the cover (1) are "flat" coupled with the tapered ends of the tapering enlarged section (12) of the watch (O)

the two basically semicircular notches (4a) obtained on the transversal edges (4) of the cover (1) exactly embrace and surround the tapered ends of the enlarged section (12) of the watch (O) from above and on the two sides.

the two longitudinal partitions (5) that protrude under the horizontal wall (2) of the cover (1) exactly engage into the corresponding slots (14) provided on the upper side of the enlarged section (12) of the watch (O) at the sides of the display of the parallelepiped block (13)

the ribs provided at the base of the longitudinal edges (3) of the cover (1) are arranged under the longitudinal centre-line (12b) of the enlarged section (12) of the watch (O).

With special reference to the latter condition, it must be noted that the longitudinal edges (3) of the cover (1), which were subject to forced divarication during the downward movement, are intrinsically flexible and spontaneously tend to recover their perfect vertical position.

Because of this tendency, the longitudinal edges (3) exert a sort of energetic embrace with respect to the enlarged section (12) of the watch (O) from opposite sides.

Considering that the ribs (3a) are situated under the centre-line (12b) of the enlarged section (12), it can be easily understood that the entire cover (1) can be uncoupled from the enlarged section (12) only by means of a new sufficiently energetic upward traction to generate a new divarication of the longitudinal edges (3).

In such a situation the function of the internal longitudinal partitions (5) of the cover (1) must be pointed out, when the same are inserted in the corresponding lateral slots (14) of the enlarged section (12) of the watch (O).

Likewise the base ribs (3a) of the longitudinal edges (3) of the cover (1) prevent the risk of accidental uncoupling, being inserted in the slots (14) of the enlarged section (12) of the watch (O), the partitions (6) prevent the cover (1) from accidentally rotating around the enlarged section (12), losing the necessary alignment between the display of the parallelepiped block (13) and the window (2a) of the cover (1).

Referring to FIG. 5, the cover of the invention (1) can be obtained according to an alternative embodiment adapted to be mounted on watches having a slightly different structure from the one illustrated in FIGS. 1 to 4. In such a case, the central enlarged section (12) of the watch (O) is centrally provided with a through axial space that cuts its entire thickness.

Said space is adapted to receive the digital component consisting in the usual parallelepiped block (13) that supports the display suitably provided in this case with height approximately equal to the height of the space.

The above is done to ensure that, also in this case, the display can protrude shortly on the outside of the space that houses the block (13).

Moreover, said block (13) is provided with a lower section having a lower width than the upper section (which supports the display) and said two sections are joined on opposite sides by means of two identical longitudinal steps (13a) with horizontal direction.

In any case, it must be noted that said block (13) is arranged inside the corresponding space in such a way that two lateral slots (14) are generated between its longitudinal walls and the sides of the space as result of possible elastic deformation imposed on the lateral walls of the space.

As mentioned above, the presence on the market of a similar is constructive embodiment of a typical "rubber" watch (O) has imposed the realisation of a dedicated embodiment (1) of said interchangeable cover.

In particular, the latter is characterised in that each vertical partition (5) is provided at the base of its internal side with a longitudinal rib (5a) with horizontal direction, and basically has the same height as the distance between the top of the parallelepiped block (13) and the height of the lateral steps (13a) of the block (13).

It appears evident that, because of the above, the cover (1) is joined directly with the parallelepiped block (13).

Because of the deep insertion of the partitions (5) inside the slots (14), as result of the intrinsic elastic deformation of said partitions (5), the longitudinal ribs (5a) are snap-fitted under the steps (13a) provided on the sides of the parallelepiped block (13), as expressly shown in FIG. 5.

The invention claimed is:

1. In combination,
a watch formed of a bracelet with a circular cross-section and a longitudinal tapering enlarged section provided on top with a space that houses a parallelepiped block containing electronic parts of the watch and having a display; and
a replaceable decorative cover for the watch,
wherein the cover comprises:
a boxed structure formed of molded plastic materials and provided with intrinsic flexibility,
said boxed structure including a wall having a longitudinally elongated window compatible with the display of the watch,
said wall bordered by two opposite pairs of downward edges including a pair of longitudinal edges and a pair of transversal edges,
the longitudinal edges provided on a lower border thereof with an inward protruding axial rib,
the transversal edges provided on a lower border thereof with a notch compatible with tapered ends of the tapering enlarged section of the watch,
a distance between the pair of longitudinal edges being less than a maximum width of the tapering enlarged section of the watch, and
the pair of longitudinal edges having a height greater than half of a thickness of the tapering enlarged section of the watch.

2. The cover as claimed in claim 1, wherein
the wall further comprises two vertical partitions protruding on an internal side of the wall and in corresponding external positions with respect to longitudinal edges of the longitudinally elongated window, and
said two vertical partitions are engaged in corresponding slots in the tapering enlarged section of the watch at sides of said parallelepiped block.

3. The cover as claimed in claim 2, wherein the vertical partitions comprise longitudinal ribs protruding horizontally at the internal side of the wall and snap-fitted under longitudinal steps provided on the sides of said parallelepiped block, after inserting said partitions inside the slots.

4. The cover as claimed in claim 1, wherein the wall further comprises two impressions in symmetrically opposite positions and having higher width and higher depth on the transversal edges of the window that is coupled with the tapered ends of the tapering enlarged section of the watch.

* * * * *